United States Patent [19]

Yang et al.

[11] Patent Number: 5,397,848
[45] Date of Patent: Mar. 14, 1995

[54] ENHANCING THE HYDROPHILICITY OF SILICONE POLYMERS

[75] Inventors: Shin-Liang S. Yang, Laguna Hills; John D. Gerace, Laguna Niguel, both of Calif.

[73] Assignee: Allergan, Inc., Irvine, Calif.

[21] Appl. No.: 65,824

[22] Filed: May 21, 1993

Related U.S. Application Data

[63] Continuation-in-part of Ser. No. 959,394, Oct. 13, 1992, Pat. No. 5,376,737, and Ser. No. 969,912, Nov. 2, 1992, Pat. No. 5,352,753, which is a continuation-in-part of Ser. No. 691,149, Apr. 25, 1991, Pat. No. 5,164,462.

[51] Int. Cl.$^6$ ............................................. C08F 283/12
[52] U.S. Cl. ................................... 525/477; 525/478; 351/160 H
[58] Field of Search ............................ 525/477, 478; 351/160 H

[56] References Cited

U.S. PATENT DOCUMENTS

| | | | |
|---|---|---|---|
| Re. 33,771 | 2/1990 | Loshaek | 526/313 |
| 4,250,268 | 2/1981 | Rody et al. | 525/100 |
| 4,316,033 | 2/1982 | Ching | 548/110 |
| 4,380,643 | 4/1983 | Yoshida et al. | 548/260 |
| 4,487,905 | 12/1984 | Mitchell | 528/15 |
| 4,528,311 | 7/1985 | Beard et al. | 524/91 |
| 4,555,545 | 11/1985 | Kimura et al. | 524/858 |
| 4,608,050 | 8/1986 | Wright et al. | 623/6 |
| 4,612,358 | 9/1986 | Beseke | 526/269 |

(List continued on next page.)

FOREIGN PATENT DOCUMENTS

| 0282294 | 9/1988 | European Pat. Off. |
| 02051542 | 2/1990 | Japan . |

OTHER PUBLICATIONS

Abstract:Thanoo et al,Tantalum loaded silicone microspheres as particulate emboli,J.Microencapsulation, 8(1), 95–101 Eng 1991.

Abstract:Mikami et al,Manufacturing method for graft polyester–silioxane,Eur. Pat. Appl. EP 400613 Dec. 5, 1990.

Abstract:Tanimori et al,Heat– and water–resistant polyester films with lower surface friction, and their manufacture. JP 02269133 Nov. 2, 1990.

Contact Lenses, A Clinical Approach to Fitting, Robert H. Hales, 59, 199–204 (1978).

Contact Lens Handbook, James R. Lee, 5, 28–32,70,71, 177.

Abstract:Efremova et al,Graft polymerization of acrylic acid as a method for producing surface layers on polycarbonate–polysiloxanes. Plast. Massy (3), 8–10- (Russ) 1990.

Abstract:Atkins et al,Low profile molding system. EP 335406 Oct. 4, 1989.

Abstract:Kim et al, Electron beam effects on polymers.11. Surface modification of Bis–GMA substrates by functionalized siloxane. J. Appl. Polym. Sci.,38(8), 1515–33 (Eng) 1989.

Abstract:NL–159124, Jan. 15, 1979, Production of hydrophilic silicone resins and rubbers.

Abstract:GB 1378971, Jan. 2, 1975, Contact lenses—from polysiloxane with grafted hydrophilic polymer surface.

Abstract:GB 1483105, Flexible silicone catheter prodn.—from radiation crosslinked parts and pref. contg. a hydrophilic polyvinyl pyrrolidone graft polymer layer, Aug. 17, 1977.

(List continued on next page.)

Primary Examiner—John C. Bleutge
Assistant Examiner—Margaret W. Glass
Attorney, Agent, or Firm—Frank J. Uxa, Jr.; Gordon L. Peterson

[57] ABSTRACT

Methods for incorporating hydrophilic constituents into silicone polymer materials are disclosed. In one embodiment, the method comprises introducing a hydrophilic component into a cross-linked and/or solid silicone polymeric material, and subjecting the hydrophilic component to conditions effective to immobilize the hydrophilic component or a hydrophilic derivative thereof and form a silicone polymer material including an effective hydrophilic constituent.

16 Claims, No Drawings

U.S. PATENT DOCUMENTS

| | | | |
|---|---|---|---|
| 4,803,254 | 2/1989 | Dunks et al. | 525/477 |
| 4,853,453 | 8/1989 | Schafer et al. | 528/28 |
| 4,868,251 | 9/1989 | Reich et al. | 525/479 |
| 4,872,877 | 10/1989 | Tiffany | 626/6 |
| 4,920,184 | 4/1990 | Schäfer et al. | 525/477 |
| 4,960,898 | 10/1990 | Sakuta et al. | 548/110 |
| 5,102,707 | 4/1992 | Canivenc et al. | 428/44 |

OTHER PUBLICATIONS

Abstract:FR 1459124, Treating polymer surfaces with mercaptosilanes and derivs thereof, 1968.

Abstract:US 3832458 Aug. 27, 1974, Hydrophilic silicone implantate—for controlled drug release.

Abstract:J51042553 Apr. 10, 1976 Silicone resin contact lenses with hydrophilic surface layer formed by low temp plasma and reinforced by graft polymer.

Abstract:US 4229273 Oct. 21, 1980, Silicone graft copolymer article contact lens-prepd. by irradiating polymer with UV light in presence of oxygen then contacting with . . . .

Abstract:FR 2407232, Hydrophilic silicone resin contact lens prodn.—by treating lens surface with gas plasma and opt. forming hydrophilic resin film by polymerization, Jun. 29, 1979.

Abstract: US 4099859, Oxygen permeable, crosslinked silicone contact lens—have a free radial polymerized, hydrophilic polymer grafted coating, Jul. 11, 1978.

Abstract:US 4131609 Dec. 26, 1978, Silicon-phthalocyanine-siloxy monomers-useful as dyes, polymer intermediates, reactive surface modifiers, etc.

Abstract: US 4806382 Feb. 21, 1989. Modifying surface of ocular implant material-by graft polymerization of vinyl pyrrolidone or hydroxyethyl methacrylate in aq. soln. using gamma irradation.

Abstract: J02145873, Wool-cloth shrink resistance process—by treating wool-cloth with corona discharge radiation and dipping in poly-dimethyl-siloxane resin, etc., Nov. 17, 1988.

Abstract: J62104975, Water-repellant textile fabric prodn.—by applying liquor contg. organo; polysiloxane and/or fluoro cpd. to fabric, low temp. plasma-treatment and applying liquor again, May 15, 1987.

Abstract:DE4019539 Jun. 19, 1990, Permanent anti-wetting coating prodn. on surface esp. of orifice plate—for ink jet printing head, by coating with silicone oil and cross-linking in plasma.

Abstract:DE 2033608, Polymeric compositions with modified surface properties, Mar. 11, 1971.

Abstract:Imai et al,Effect of mobile molecular chains on cell attachment and growth, Kobunshi Ronbunshu, 42(11), 713–18(Japan) 1985.

Abstract:Samu et al,UV-curable silicone compositions containing surface-treated fibers, JP 86–135636, Jun. 11, 1986.

Abstract:Kawakami et al, Synthesis of silicone graft polymers and their surface active properties, Makromol. Chem. 185(1),9–18(Eng) 1984.

Abstract:Kawakami et al,Surface active properties of silicone-containing polymers,Polym. Bull.(Berlin),10-(7–8), 368–71 (Eng, 1983).

Abstract: Kawakami et al,Synthesis and applications of polysiloxane macromers,ACS Symp. Ser., 286(Ring-Opening Polym), 245–61 (Eng) 1985.

Abstract:Pinchuk et al,The use of silicone/polyurethane graft polymers as a means of eliminating surface cracking of polyurethane prostheses, J. Biomater.Appl., 3(2),260–96 (Eng) 1988.

Abstract:JP 63162878; Surface modification of siloxane-containing polymers.

Abstract:JP 87–126042 May 25, 1987; Siloxane block polymers as waterproofing finishes for polymers.

Abstract: EP 88–303172 Apr. 8, 1988, Intraocular implants having graft polymerized surfaces with increased hydrophilicity and reduced adhesion.

Abstract:US 3959102, May 25, 1976: Hydrophilic concavo-convex contact lens-water-containing crosslinked silicone polyvinylpyrrolidone graft copolymer.

Abstract:US 3632715 Oct. 21, 1964;Modifying surface props of vinylic polymers—by treatment with a fluid organosilicon cpd.

Abstract:FR 2088597 Apr. 17, 1970; Grafted silicone resins—with vinyl pyrrolidone by heating.

ENHANCING THE HYDROPHILICITY OF SILICONE POLYMERS

RELATED APPLICATION

This application is a continuation-in-part of application Ser. No. 959,394, filed Oct. 13, 1992, now U.S. Pat. No. 5,376,737 and of application Ser. No. 969,912, filed Nov. 2, 1992, now U.S. Pat. No. 5,352,753 each of which, in turn, is a continuation-in-part of application Ser. No. 691,149, filed Apr. 25, 1991, now U.S. Pat. No. 5,164,462. Each of these applications and the above-noted patent is incorporated in its entirety herein by reference.

BACKGROUND OF THE INVENTION

This invention relates to benefitting polymeric materials. More particularly, this invention relates to methods for incorporating hydrophilic constituents into silicone polymer materials to provide effectively enhanced hydrophilic polymer materials useful, for example, as lenses. New silicone polymer materials and intraocular lenses (IOLs) made therefrom are also included.

Silicone polymers are quite effective as materials for various ophthalmic devices, such as contact lenses and IOLs. These silicone polymeric materials have very useful physical and optical properties making them advantageous for use in such devices. One property that exists in certain such materials is high hydrophobicity.

Increasing the hydrophilicity of silicone polymer materials can involve providing a hydrophilic component on the surface or surfaces of a lens made from such materials. Such surface coatings tend to be removed after a relatively short period of use. Other approaches to increasing the hydrophilicity of silicone materials can be complex and/or result in an inadequate and/or uncontrolled increase in hydrophilicity.

Clearly, it would be advantageous to provide new methods for incorporating hydrophilic constituents into silicone polymer materials, and new hydrophilic silicone polymer materials and IOLs made therefrom.

SUMMARY OF THE INVENTION

New methods for incorporating hydrophilic constituents into silicone polymer materials, hydrophilic silicone polymer materials and IOLs made therefrom have been discovered. The present methods provide for the simple and straightforward inclusion of controlled amounts of hydrophilic constituents in silicone polymer materials. The hydrophilic constituents are included in the silicone polymer material, preferably substantially uniformly distributed in the silicone polymer material, as to provide a material with enhanced hydrophilicity, for example, relative to a substantially identical polymer material without the hydrophilic constituent. The present methods are relatively easy to practice and control, and provide silicone polymer materials having advantageously long lasting hydrophilicity. Such hydrophilic silicone polymer materials, particularly such materials which are optically clear, are very useful included in the optics of IOLs.

In one broad aspect, the present methods for incorporating a hydrophilic constituent into a silicone polymer material comprise introducing a hydrophilic component including a hydrophilic portion and a silicone polymer portion into a silicone polymeric material, preferably a cross-linked and/or solid silicone polymeric material. The hydrophilic component is subjected to conditions effective to immobilize the hydrophilic component or a hydrophilic derivative thereof, and form a silicone polymer material including a hydrophilic constituent in an amount effective to provide increased hydrophilicity to the silicone polymer material, for example, relative to a substantially identical polymer material without the hydrophilic constituent. The increased hydrophilicity provided may be relative to the silicone polymeric material prior to the inclusion of the hydrophilic constituent.

In another broad aspect of the present invention, a precursor mixture is formed. This precursor mixture comprises two or more silicon-containing components, e.g., pre-polymers (base polymers), cross-linking agents, fillers, silicone reinforcing resins and the like and mixtures thereof, in amounts effective to chemically react and form a silicone polymeric material, and a hydrophilic component, as described above. This precursor mixture is subjected to conditions effective to chemically react the silicon-containing components, immobilize the hydrophilic component or a hydrophilic derivative thereof, and form a silicon polymer material including a hydrophilic constituent in an amount effective to provide enhanced hydrophilicity to the silicone polymer material, for example, relative to a substantially identical silicone polymer material without the hydrophilic constituent.

One important feature of the present invention is the use of a hydrophilic component which includes both a hydrophilic portion and a silicone polymer portion. Without wishing to limit the present invention to any particular theory of operation, it is believed that the silicone polymer portion of the hydrophilic component facilitates effective and efficient combining of the hydrophilic component with the silicone polymeric material or the silicon-containing components. In other words, it is believed that the silicone polymer portion allows the hydrophilic component to be more compatible with, for example, more easily dispersed in, the silicone polymer material or silicon-containing components, for example, relative to a substantially identical hydrophilic component without the silicone polymer portion. This, in turn, is believed to facilitate allowing the hydrophilic component to provide the desired degree of hydrophilicity, preferably substantially without detrimentally affecting the properties of the original silicone polymeric material. Silicone polymer materials which are very well suited for their intended purpose, for example, for the production of ophthalmic devices, such as corneal contact lenses, IOLs, and corneal intrastromal implant lenses, are obtained.

DETAILED DESCRIPTION OF THE INVENTION

The present invention is applicable to increasing the hydrophilicity of any silicone polymeric material.

For example, any cross-linked and/or solid silicone polymeric material may be processed in accordance with the present invention. For example, the silicone polymeric material may or may not include reactable groups.

As used herein, the term "reactable groups" refers to substituents on the silicone polymeric material or one of the silicon-containing components of the presently useful precursor mixtures which are capable of being reacted with a reactable hydrophilic component. Examples of such reactable groups include hydride groups, groups which include carbon-carbon unsaturation, hydroxyl groups, carboxyl groups, amine groups, epoxide groups, other carbon-containing groups, other nitrogen-containing groups, phosphorus-containing groups, sulfur-containing groups, halogen-containing groups, free radicals and the like and mixtures thereof. The present invention is particularly applicable when the reactable groups are selected from hydride groups and groups containing carbon-carbon unsaturation, more preferably when the reactable groups are hydride groups. Such reactable groups may be, and often are, the same type of groups which are reacted to form the silicone polymeric material. Thus, the silicone polymeric material may include residual reactable groups.

However, it is not necessary that the silicone polymeric material include reactable groups or that the hydrophilic component chemically react with the silicone polymeric material or one of the silicon-containing components of the presently useful precursor mixtures. Thus, although such chemical reaction can occur to immobilize a hydrophilic derivative of the hydrophilic component, silicone polymer materials including physically immobilized hydrophilic components may also be obtained in accordance with the present invention. Again, without wishing to limit the invention to any particular theory of operation, it is believed that the silicone polymer portion of the presently useful hydrophilic constituents, e.g., the hydrophilic component itself, often have sufficiently high molecular weight so as to facilitate the physical immobilization of the hydrophilic component in the silicone polymer material. Therefore, the hydrophilic constituent may be physically and/or chemically immobilized in the silicone polymer material. The hydrophilic components employed may be reactable or non-reactable with the silicone polymeric material or silicon-containing components of the presently useful precursor mixtures.

The base silicone polymeric materials which may be used in the present methods may be chosen from any suitable such materials, for example, the polymeric materials described in Travnicek U.S. Pat. Nos. 3,996,187, and 3,996,189, Reich et al U.S. Pat. No. 4,868,251, and Mbah U.S. Pat. No. 4,882,398, as well as other prior art materials. The silicone polymeric material is preferably cross-linked and/or is present in the solid phase prior to being exposed to the hydrophilic component in accordance with the present invention. The polymeric material can be cured (cross-linked) using any suitable technique, for example, peroxide initiation, platinum catalysis and the like. In a particularly useful embodiment, the present processing to incorporate a hydrophilic constituent into a silicone polymer material, for example, the present subjecting step, does not substantially increase or decrease, that is substantially ineffective to increase or decrease, the degree of polymerization or cross-linking of the silicone polymeric material into which the hydrophilic component is introduced. The present processing preferably has little or no effect, other than to provide the desired hydrophilicity on the properties of the final silicone polymer material. The silicone polymer materials produced in accordance with the present methods are preferably utilized in medical devices, for example, as lens materials, such as foldable IOL optic materials, without further substantial polymerization or cross-linking.

The hydrophilic component is chosen (1) to provide the desired hydrophilicity to the silicone polymer material when incorporated into the silicone polymer material; or (2) to yield a hydrophilic constituent which provides the desired hydrophilicity to the silicone polymer material when incorporated into the silicone polymer material and to react with the reactable groups present in the silicone polymeric material or in at least one of the silicon-containing components of the presently useful precursor mixture. It should be noted that providing silicone polymer materials, particularly silicone polymer materials which are optically clear and are useful for ophthalmic devices, such as corneal contact lenses, IOLs, corneal intrastromal lenses and the like, with enhanced hydrophilicity is an important application of the present invention.

In one embodiment, the present invention relates to methods for incorporating a hydrophilic constituent component into a silicone polymer material. These methods comprise introducing a hydrophilic component containing a hydrophilic portion and a silicone polymer portion into a hydrophilic polymeric material, preferably a cross-linked and/or solid silicone polymeric material; and subjecting the hydrophilic component to conditions effective to immobilize the hydrophilic component or a hydrophilic derivative thereof and form a silicone polymer material including a hydrophilic constituent, preferably in an amount effective to provide enhanced or increased hydrophilicity to the polymer material, for example, relative to a substantially identical polymer material without the hydrophilic constituent.

In another embodiment, the present methods comprise forming a precursor mixture containing two or more silicon-containing components in amounts effective to chemically react and form a silicone polymeric material, and a hydrophilic component, as described herein. This precursor mixture is subjected to conditions, e.g., polymerization conditions, effective to chemically react the two or more silicon-containing components, immobilize the hydrophilic component or hydrophilic derivative thereof, and form a silicone polymer material including a hydrophilic constituent, preferably in an amount effective to provide enhanced or increased hydrophilicity to the polymer material, for example, relative to a substantially identical silicone polymer material without the hydrophilic constituent.

The introducing, forming and subjecting steps of the present methods are preferably effective to distribute the hydrophilic constituents substantially uniformly throughout the silicone polymer materials.

The hydrophilic component can be introduced into the silicone polymeric material or into one or more components of the presently useful precursor mixtures combined with a liquid carrier, for example, in the form of a suspension or dispersion in a liquid medium or, and preferably, in the form of a solution. The liquid medium or solvent should be selected to be compatible with (i.e., have no undue detrimental effect on) the hydrophilic component and the silicone polymeric material or precursor mixture, and is preferably such that it can be easily removed from the silicone polymeric material, the precursor mixture or the silicone polymer material. A particularly useful class of liquid carriers, for example, when siloxane polymers are involved, are hydrocarbon-based materials, such as isopropyl alcohol, tetrahydrofuran, hexane, aromatic hydrocarbon-based materials, for example, toluene, and the like.

The amount of hydrophilic component introduced into the polymeric material or into one or more components of the presently useful precursor mixtures should be sufficient to provide the desired benefit, e.g., enhanced hydrophilicity, to the silicone polymer material. Some excess of hydrophilic component may advantageously be introduced to facilitate, for example, increase, the rate at which the hydrophilic component is immobilized and/or chemically reacts with the silicone polymeric material or with one or more components of the precursor mixture. The amount of hydrophilic constituent included in the final silicone polymer material varies widely depending on the specific hydrophilic constituent involved and the degree of hydrophilicity desired. For example, the amount of hydrophilic constituent in the silicone polymer material can range from about 0.01% or less to about 1% or about 5% or about 10% or more, by weight.

In any event, the hydrophilic component which is combined with the silicone polymeric material or the precursor mixture is subjected to conditions effective to immobilize and/or chemically react this component and form a hydrophilic constituent in the resulting silicone polymer material which is the hydrophilic component and/or is derived from the hydrophilic component. In one embodiment, the hydrophilic constituent is covalently bonded into the silicone polymer material.

The introducing, forming and subjecting steps of the present invention can occur sequentially (introducing or forming before subjecting) or simultaneously or a combination thereof, for example, with these two steps occurring at least partially simultaneously and the subjecting step continuing after the introducing or forming step is concluded.

The conditions at which the above-noted subjecting step occurs are chosen to provide the desired final product. These conditions are preferably such that the silicone polymeric material, when present, and final silicone polymer material suffer no substantial detrimental effects. For example, such conditions are preferably selected so that no substantial increase or decrease in the degree of polymerization or the degree of cross-linking of the silicone polymeric material occurs. Often, such conditions are selected to maintain the silicone polymeric material and final silicone polymer material in a solid state. When the precursor mixtures are employed, the subjecting conditions can be selected from conditions, for example, conventional conditions, known to be useful to chemically react or polymerize (for example, cross-link) the silicon-containing components of the precursor mixtures. Subjecting temperatures are preferably in the range of about 0° C. to about 150° C., more preferably in the range of about 20° C. to about 100° C. or about 110° C. Subjecting times may vary widely. For example, times on the order of 0.1 or about 0.5 hours or less to about 70 hours or more may be employed. Particularly useful results are obtained where the subjecting time is in the range of about 2 hours or about 4 hours to about 12 hours to about 24 hours.

The subjecting step may be catalyzed or promoted so as to facilitate covalent bonding of the hydrophilic constituent to the silicone polymer material and/or the reaction, e.g., polymerization or cross-linking, of the silicon-containing components of the precursor mixture. Although an effective amount of a suitable separate or additional catalyst or promotor can be incorporated into the silicone polymeric material before and/or during the subjecting step, it has unexpectedly been found that the catalyst or promotor used to facilitate the formation of the polymeric material, which is present in the polymeric material, is often effective to promote the chemical reaction or covalent bonding of the hydrophilic constituent to the silicone polymer material. Such "residual" catalysis is very convenient, for example, requiring that no separate or additional catalyst or promotor be used, and provides for effective hydrophilic constituent/polymer material covalent bonding at relatively mild conditions. Conducting the present subjecting step at mild or low severity conditions also reduces the risks that the silicone polymer material will be detrimentally affected by such processing.

A particularly useful class of polymerization catalysts which also can act to promote the hydrophilic constituent/silicone polymer material covalent bonding and/or the reaction, e.g., polymerization or cross-linking of the silicon-containing components of the precursor mixture is the platinum group metal-containing components, preferably platinum-containing components, utilized in promoting hydrosilylation (polymerization) or cross-linking, for example, the formation of silicone polymers. Many platinum group metal-containing components are conventional and well known as hydrosilylation (polymerization) catalysts.

The platinum group metal-containing components have been found to be particularly effective when the reactable hydrophllic component includes a functional group selected from hydride groups or functional groups containing carbon-carbon unsaturation and the reactable groups of the polymeric material or one of the silicon-containing components of the presently useful precursor mixtures are selected from the other of such groups. For example, if the reactable hydrophilic component includes a functional group containing carbon-carbon unsaturation, the reactable groups of the polymeric material or one of the silicon-containing components are hydride groups, and vice versa.

After the subjecting step, the resulting silicone polymer material may be processed to remove any free hydrophilic component. For example, this silicone polymer material may be extracted with one or more non-interfering or compatible materials to extract the free hydrophilic component from the polymer material. The remaining hydrophilic constituent is effective to provide the desired hydrophilicity to the polymer material.

In one embodiment, the silicone polymeric material, preferably a solid and cross-linked polymeric material, is pre-formed into a useful product, e.g., IOL, before being processed in accordance with the present invention. The final silicone polymer material which is produced has enhanced hydrophilicity and is suitable for use, for example, as an IOL.

In another embodiment, the present subjecting step occurs such that the precursor mixture (silicon-containing components and hydrophilic component) is processed, for example, using one or more techniques such as injection molding, to form a silicone polymer material having enhanced hydrophilicity and formed into a useful product, e.g., IOL. The final silicone polymer material is suitable for use, for example, as an IOL.

Alternately, a quantity of the final silicone polymer material is processed, e.g., using conventional techniques, into a useful product after the subjecting step. For example, conventional lens manufacturing and/or finishing techniques can be employed to produce a corneal contact lens, IOL or corneal intrastromal lens having effective hydrophilicity from the presently derived final silicone polymer material.

The present invention is particularly applicable in situations in which the physical/optical properties of the silicone polymer materials should be closely controlled in order to achieve a useful product. One specific example of such a situation is the formation of a foldable IOL, that is an IOL which is deformable for insertion through a small, e.g., about 3 mm in length, surgical incision. The configuration of the foldable IOL, in particular the optical resolution of the foldable IOL, should return completely in a reasonable time after the lens is placed in the eye. Thus, a foldable IOL should be made of a material which is elastomeric and has consistent and homogeneous composition throughout the cross-linked network polymeric structure.

The present invention allows a silicone polymer material having advantageously enhanced hydrophilicity to be produced under closely controlled conditions. The hydrophilic constituent can be incorporated into the already formed silicone polymeric material in accordance with the present invention. In this particularly useful aspect of the invention, the polymeric material is formed without interference from the hydrophilic component. By incorporating a hydrophilic component or hydrophilic derivative thereof, a silicone polymer material with the desired degree of hydrophilicity is obtained. The resulting silicone polymer material is preferably formable into a foldable IOL.

Specific examples of useful silicone polymeric materials are those materials identified as cross-linked silicone elastomers derived from vinyl functional siloxane pre-polymers (base polymers) and hydride functional cross-linking agents or components. Such vinyl functional siloxane base polymers and hydride functional cross-linking components are particularly useful as silicon-containing components in the presently useful precursor mixtures.

In one embodiment, such base polymers have the following structure or formula:

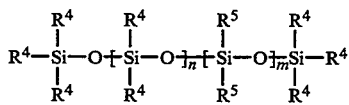

and mixtures thereof, wherein each $R^4$ and $R^5$ is independently selected from the group consisting of H, $CH=CH_2$, alkyl radicals, substituted alkyl radicals, alkoxy radicals, substituted alkoxy radicals, alkenyl radicals with a terminal double bond, substituted alkenyl radicals with a terminal double bond, aryl radicals, substituted aryl radicals and fluoro radical, provided that at least one, and preferably at least two, of the $R^4$s is selected from H and olefinically unsaturated groups; and n and m each is an integer independently selected from integers in the range of 0 to about 20,000. In the event that one or more $R^4$s and/or $R^5$s are fluoro radicals, one or more other $R^4$s and/or $R^5$s are preferably organic radicals. One or more of the $R^4$s and/or $R^5$s may be organo fluoro radicals, for example, fluoro hydrocarbon radicals. In one embodiment, each of the $R^4$s, other than those which are selected from H and olifinically unsaturated groups, and the $R^5$s is methyl. Each of the $R^4$s and $R^5$s may be independently selected from alkyl radicals containing 1 to about 4 carbon atoms, fluoro alkyl radicals containing 1 to about 3 carbon atoms, phenyl radicals, substituted aryl radicals, alkenyl radicals containing 2 to about 4 carbon atoms and having a terminal double bond and mixtures thereof.

Examples of useful alkenyl groups include ethenyl, propenyl, butenyl, hexenyl, octenyl and the like.

The cross-linking or cross-linker agents useful with such base pre-polymers are preferably components of a two part, silicone elastomer formulation, more preferably a two part, platinum catalyzed vinyl/hydride, addition cured silicone elastomer formulation. Thus, when the base pre-polymer is vinyl functional, the cross-linking agent is hydride functional. In addition, one or more of the base pre-polymer and the cross-linking agent can be both vinyl and hydride functional.

In any event, the silicone elastomer is cross-linked and optically clear. These optically clear elastomeric compositions are very effective for inclusion in corneal contact lenses, IOLs and corneal intrastromal lenses. Conventional lens forming techniques, for example, molding techniques, can be used to provide lenses or lens blanks from such elastomeric compositions. These lenses or lens blanks can then be processed in accordance with the present invention to provide the desired hydrophilicity.

The preferred siloxane cross-linking agents include a plurality of, for example, at least three (3), functional groups per molecule.

Suitable cross-linking agents include agents which are conventionally used to produce cross-linked silicone polymers, in particular, polysiloxane elastomers, for example, employing two part platinum catalyzed silicone systems to produce silicone elastomers by vinyl/hydride addition curing. Thus, suitable cross-linking agents are available as a component of many such conventional two part systems. Specific examples of effective cross-linking agents include 1,3,5,7-tetramethylcyclo-tetrasiloxane, methyl hydropolysiloxane, 1,3,5-trivinyl-1,1,3,5,5-pentamethyl-trisiloxane, methyl vinyl polysiloxane and the like.

The relative amounts of base pre-polymer and cross-linking agent employed to produce the siloxane elastomer composition are chosen to provide a cross-linked polymeric material having the desired properties, including the desired degree of cross-linking. The relative amounts of the components utilized varies depending on many factors, for example, on the specific components being employed, and on the application for which the polymeric material is to be employed. As noted above, conventional two part silicone polymer formulations can be employed.

In a particularly useful embodiment of the present invention, the ratio of monomers (or prepolymers) used is chosen to provide a predetermined concentration of reactable groups in the polymeric material or precursor mixture. This predetermined concentration is preferably greater than the concentration of reactable groups in a substantially identical polymeric material or precursor mixture for use without processing in accordance with the present invention. Such greater concentration of reactable groups advantageously facilitates the chemical reaction of the reactable hydrophilic component with the reactable groups of the polymeric material or of the silicon-containing component or components of the precursor mixture. However, any adjustments to the conventional two part silicone polymer formulations (in terms of relative amounts of components) are relatively minor (if required at all). For example, if the conventional weight ratio of part A to part B is 1:1, such ratio is preferably adjusted, if at all, to be within the range of about 0.75:1 to about 1 to 0.75 to facilitate incorporation of the hydrophilic constituent.

Any suitable hydrophilic component may be employed in the present invention, provided that such component includes a hydrophilic portion and a silicone polymer portion, and such hydrophilic component functions as set forth herein. The hydrophilic portion of the hydrophilic component should be such as to provide the desired degree of hydrophilicity of the silicone polymer material into which the hydrophilic component or hydrophilic derivative thereof is incorporated. The hydrophilic portion of the hydrophilic component may be included as a single hydrophilic group or as a plurality of hydrophilic groups bonded, preferably covalently bonded, to the silicone polymer portion of the hydrophilic component.

Examples of hydrophilic groups which may comprise the hydrophilic portion of the hydrophilic component include various hydrophilic polymers, oligomers and hydrophilic moieties which have been characterized as polyelectrolytes, surfactants and/or thickeners depending upon their chemical structures and applications. These include synthetically derived groups, naturally occurring groups and synthetically modified naturally occurring groups. Some specific examples include polyvinylpyrrolidone, polyacrylic acid, polyethylene oxide, polypropylene oxide, polyvinyl pyridine, polysaccharides, polycarboxyl methyl cellulose, polymethylacrylic acid, polyacrylamide, polypeptides, poly sodium styrene sulfonate, polyvinyl alcohol, polyhydroxyethyl methacrylate, heparin and the like and mixtures thereof. These groups may be substituted with substituents including one or more of carbon, hydrogen, oxygen, halogen, phosphorus, nitrogen, sulfur and the like, provided that such substituent does not substantially adversely affect the properties and functioning of the silicone polymer material into which the hydrophilic constituent is incorporated. Particularly useful groups included in the hydrophilic portion of the presently useful hydrophilic components include polyalkylene oxide groups containing two to about six carbon atoms per alkylene moiety. Preferred polyalkylene oxide groups include polyethylene oxide and polypropylene oxide groups, especially polyethylene oxide groups. The hydrophilic component may be, and preferably is, a copolymer, for example, a block copolymer, a graft copolymer and the like, comprising one or more hydrophilic groups making up the hydrophilic portion and one or more silicone polymer groups making up the silicone polymer portion.

The silicone polymer portion of the presently useful hydrophilic components may be selected from any suitable type of silicone polymer or silicone polymer group. Preferably, the type of silicone polymer employed in the silicone polymer portion of the presently useful hydrophilic components is similar to that in the presently useful silicone polymeric materials, for example, cross-linked and/or solid silicone polymeric materials, or in the presently useful precursor mixtures. For example, if the base polymer is a polydimethylsiloxane, it is preferred that the silicone polymer portion of the hydrophilic component be a polydimethylsiloxane. If the base polymer is a polydimethyldiphenyl siloxane copolymer, it is preferred that the silicone polymer portion have a similar mole percentage ratio of dimethyl siloxane and diphenyl siloxane units. Such similarity enhances the compatibility between the hydrophilic component and the silicone polymeric material or the precursor mixture.

In one embodiment, the silicone polymer portion of the hydrophilic component has sufficiently high molecular weight so as to facilitate the physical immobilization of the hydrophilic constituent in the silicone polymer material.

In another embodiment, the hydrophilic portion and/or the silicone polymer portion of the hydrophilic component includes functional groups which react with reactable groups present in the silicone polymeric material or in the precursor mixture. The reactable groups on the silicone polymeric material and/or the functional groups on the hydrophilic component are formed in situ, for example, by high energy radiation. Such functional groups, for example, free radicals, react with the reactable groups present in the silicone polymeric material or the precursor mixture to provide very effective covalent bonding of the hydrophilic constituent in the silicone polymer material.

Alternately, the hydrophilic portion of the hydrophilic component may contain vinyl groups which react with residual hydride groups present in the silicone polymeric material to covalently bond the hydrophilic component in the silicone polymer material.

Many examples of the presently useful hydrophilic components are commercially available. Therefore, a detailed description of the manufacture of such components is not presented here, and is not considered a part of the present invention.

The present silicone polymer materials may include one or more other beneficial components in amounts effective to provide desired beneficial properties to the material. An example of such a beneficial component is an ultraviolet light absorbing component.

The following non-limiting examples illustrate certain aspects of the present invention.

EXAMPLES 1 to 5

A series of tests was performed to determine if addition cured polysiloxane polymers could be provided with enhanced hydrophilicity.

Five (5) solid slabs of a conventional platinum-catalyzed, addition cure, cross-linked polyorganosiloxane polymer were provided. These optically clear polymer slabs were derived through a thermally cured process from a conventional 50:50 (by weight) Part A/Part B mixture, for example, a Part A and Part B combination sold by Shin-Etsu Chemical Company Limited under the trademark KE-1935.

Each of these cured slabs was extracted in isopropanol and had dimensions approximately 2 cm in diameter by 2 cm thick. Each of the slabs was weighed. A solution of 10% (dry weight) of a hydrophilic component, an ethylene oxide/polydimethyl siloxane copolymer (sold by Huls under the trademark PS-071), in tetrahydrofuran (THF) was prepared.

One of the slabs, identified as Slab 1, was not subjected to any treatment with the solution. Each of the other slabs was placed in a separate vial. Approximately 15 ml of the THF solution was added to each of these vials. Slab 1 was placed in a vial and approximately 15 ml of 100% THF was added.

Each of the slabs was allowed to soak for approximately 24 hours. Afterwards, the THF was decanted from each vial. The slabs were then allowed to dry at atmospheric pressure and room temperature for 18 hours.

Each of the dried slabs was placed in a vial and washed, employing vigorous shaking, with deionized water. This deionized water wash and shaking were repeated three additional times with each slab. The slabs were allowed to dry at atmospheric pressure and 45° C. for 18 hours. The slabs were then cooled to room temperature. The surfaces of the slabs were then dried with a clean, lint-free wipe. Each of the slabs was weighed again.

Slabs 4 and 5 were subjected to gamma radiation at 3.2 mRad. An extraction apparatus was set up using 450 water as the extraction medium. All of the slabs, that is Slabs 1 to 5, were extracted at 45° C. in deionized water for seven (7) days. After extraction, each of the slabs was weighed again.

Results of these tests are as follows:

| SLAB NO. | INITIAL WEIGHT | WEIGHT AFTER WATER WASHING | WEIGHT GAIN | ADDITIVE PRESENT | WEIGHT AFTER EXTRACTION | ADDITIVE PRESENT AFTER EXTRACTION |
|---|---|---|---|---|---|---|
| 1 | 0.5889 | 0.5884 | 0 | 0.0% | 0.5888 | 0.0% |
| 2 | 0.6138 | 0.6390 | 0.0252 | 4.1% | 0.6345 | 3.4% |
| 3 | 0.5980 | 0.6211 | 0.0231 | 3.9% | 0.6174 | 3.2% |
| 4 | 0.4858 | 0.5063 | 0.0205 | 4.2% | 0.5032 | 3.6% |
| 5 | 0.5280 | 0.5488 | 0.0208 | 3.9% | 0.5455 | 3.3% |

The hydrophilicity of each of the extracted slabs was determined by a sessile drop contact angle test. Results of these tests are as follows:

| SLAB NO. | MEASUREMENT 1 | MEASUREMENT 2 | MEASUREMENT 3 | AVG | STANDARD DEVIATION |
|---|---|---|---|---|---|
| 1 | 102 | 105 | 104 | 104 | 1.5 |
| 2 | 18 | 13 | 15 | 15 | 2.5 |
| 3 | 20 | 19 | 20 | 20 | 0.6 |
| 4 | 14 | 16 | 16 | 15 | 1.2 |
| 5 | 15 | 13 | 15 | 14 | 1.1 |

These results indicate that the above-described procedures are effective to provide enhanced hydrophilicity. The extraction process removed excess hydrophilic material present and loosely attached to the silicone surface. The majority of the hydrophilic component however is physically immobilized in the silicone material. Gamma radiation may provide covalent bonding between the hydrophilic component and the polyorganosiloxane polymer. The treated slabs (Slabs 2 to 5) do retain a significant hydrophilic characteristic after aqueous extraction at 45° C. over one week. Each of the extracted slabs was optically clear, making the treatment methodologies and the resulting slabs useful in the production of IOLs.

EXAMPLES 6 TO 14

A large slab of the platinum-catalyzed, addition cure, cross-linked polyorganosiloxane polymer used in Examples 1 to 5 was provided. Small pieces were cut from this slab with a razor blade. The pieces were approximately 1 cm by 1 cm by 2 cm.

Nine (9) sample vials with screw caps were provided. A piece of the polymer was added to each vial.

In each of the first three vials, carrying Samples (polymer pieces) 6 to 8, a solution of 10% by weight of an ethylene oxide/dimethyl siloxane copolymer (sold by Huls under the trademark PS-071) in THF was added. The vials were capped.

In each of the next three vials, carrying Samples (polymer pieces) 9 to 11, a solution of 20% by weight of an ethylene oxide/dimethyl siloxane copolymer (sold by Huls under the trademark PS-071) in THF was added. The vials were capped.

In the last three vials, carrying Samples (polymer pieces) 12 to 14, a solution of 10% by weight of a propylene oxide/dimethyl siloxane copolymer (sold by Huls under the trademark PS-072) in THF was added. The vials were capped.

Each of the polymer pieces was allowed to soak in the THF solutions for 24 hours. Observations were made of the appearance of the solutions and samples.

Each of the polymer pieces was removed from the THF solution and placed in a clean, labeled vial to dry.

Each polymer piece was allowed to dry in a fume hood for 48 hours. Each of the polymer pieces was then washed with running deionized water for approximately 15 seconds and placed in clean, dry, labeled vial.

The vials (containing the polymer pieces) were then placed in a 45° C. oven for 30 minutes to dehydrate the polymer pieces.

The surface hydrophilicity of each polymer piece was then assessed by sessile drop contact angle measurements with water.

The results of these tests are as follows:

After incubation in the THF solution, Samples 6 to 8 appear to have swelled the most, Samples 9 to 11 did swell significantly; and Samples 12 to 14 did not swell significantly. Each solution appeared to be cloudy.

After removing the Samples (polymer pieces) from the THF solution, they all appeared cloudy with an "oily" surface.

After washing the Samples with deionized water, each Sample became very clear and clean.

The results of the sessile drop contact angle measurements are provided below:

| SESSILE DROP CONTACT ANGLE MEASUREMENTS | | | | |
|---|---|---|---|---|
| SAMPLE | 1 | 2 | 3 | 4 |
| CONTROL A(1) | 61 | 97 | 85 | 96 |
| CONTROL B(2) | 107 | 115 | 122 | 127 |
| 6 | 13 | 10 | 13 | 13 |
| 7 | 11 | 14 | 11 | 9 |
| 8 | 10 | 13 | 8 | 9 |
| 9 | 14 | 13 | 15 | 10 |
| 10 | 11 | 9 | 10 | 14 |
| 11 | 14 | 10 | 9 | 10 |
| 12 | 65 | 55 | 58 | 68 |
| 13 | 66 | 50 | 48 | 58 |
| 14 | 89 | 95 | 96 | 95 |

(1) Control A and B were pieces of polymer which were subjected to the same treatment described above except that pure THF was used in each case.

After washing and drying, the treated polymer pieces showed significant reductions in contact angles. This enhanced hydrophilicity is particularly significant with Samples 6 to 11. Although some hydrophilicity enhancement is achieved in Samples 12 to 14, such enhancement is not as substantial as in the other samples. Each of the Samples 6 to 14 is optically clear and useful in the production of IOLs. That is, slabs of material identical to the materials of each of Samples 6 to 14, particularly Samples 6 to 11, can be machined and/or otherwise processed, using conventional techniques, into IOLs having the enhanced hydrophilicity apparent in the corresponding Sample.

EXAMPLE 15

A quantity of Part A and Part B of a platinum-catalyzed, addition cure, cross-linked polyorgano siloxane polymer was provided. In addition, a quantity of ethylene oxide/dimethyl siloxane copolymer, sold by Huls under the trademark PS-071, was provided.

A quantity of this copolymer was added to Part A so that the combination included 4% by weight of the copolymer. This combination was mixed thoroughly, and then centrifuged and degassed at 2000 RPM for 30 minutes.

This modified Part A was mixed with Part B at a 1:1 weight ratio. The mixture was centrifuged and degassed at 2000 RPM for 30 minutes. The mixture was then poured into a glass slab mold and cured at 80° C. for 18 hours.

The cured slab was removed and the sessible drop contact angle was measured to determine the degree of hydrophilicity.

The addition of the hydrophilic copolymer to Part A caused the consistency of the fluid Part A to change dramatically. The consistency was thicker than before. The fluid coalesced more, but remained clear.

The cured slab appeared to have a very clear (optically clear), clean, smooth surface. Upon wetting the cured slab, it was observed to have a slicker appearance (relative to a similar slab without the hydrophilic copolymer) indicating an increase in hydrophilicity. Sessile drop contact angle measurements of the slab indicated that the contact angle was 40±5 degrees. This cured slab was optically clear, and is useful in the production of IOLs. For example, the cured slab can be machined and/or otherwise processed, using conventional techniques, into an IOL having the enhanced hydrophilicity apparent in the cured slab. This IOL has enhanced hydrophilicity apparent in the cured slab. Alternatively, the mixture can be injection molded directly into an IOL or other articles which exhibit the desired degree of hydrophilicity.

While this invention has been described with respect to various specific examples and embodiments, it is to be understood that the invention is not limited thereto and that it can be variously practiced within the scope of the following claims.

What is claimed is:

1. A method for incorporating a hydrophilic component into a silicone polymer material which comprises:
   introducing a hydrophilic component into a silicone polymeric material selected from the group consisting of cross-linked silicone polymeric materials and solid silicone polymer materials, said hydrophilic component including a hydrophilic portion and a silicone polymer portion; and
   subjecting said hydrophilic component and said silicone polymeric material to conditions effective to physically immobilize at least a portion of said hydrophilic component and form a silicone polymer material which is optically clear and includes said hydrophilic component physically immobilized in and distributed throughout said silicone polymer material in an amount effective to provide increased hydrophilicity to said silicone polymer material relative to a substantially identical polymer material without said hydrophilic component, provided said subjecting is ineffective to increase or decrease the degree of polymerization or the degree of cross-linking of said silicone polymeric material, and said silicone polymer material is utilized without further substantial polymerization or cross-linking.

2. The method of claim 1 wherein said introducing and subjecting are effective to distribute said hydrophilic component uniformly throughout said silicone polymer material and said silicone polymer material is sufficiently elastomeric to produce an optic of a foldable intraocular lens therefrom.

3. The method of claim 1 wherein said silicone polymeric material is cross-linked and solid, and said silicone polymer portion is effective to enhance the compatibility of said hydrophilic component with said silicone polymeric material relative to a substantially identical hydrophilic component without said silicone polymer portion.

4. The method of claim 1 wherein said silicone polymeric material is an optically clear, addition-cure, cross-linked polysiloxane polymer, said silicone polymer material is elastomeric, and which further comprises forming said silicone polymer material into an optic of a foldable intraocular lens.

5. A method for incorporating a hydrophilic constituent into a silicone polymer material which comprises:
   introducing a hydrophilic component including a hydrophilic portion and a silicone polymer portion into a silicone polymeric material selected from the group consisting of cross-linked silicone polymeric materials and solid silicone polymeric materials so as to distribute said hydrophilic component throughout said silicone polymer material; and
   subjecting said hydrophilic component and said silicone polymeric material to conditions effective to chemically react said hydrophilic component with said silicone polymeric material, thereby forming a silicone polymer material which is optically clear and includes a covalently bonded hydrophilic constituent derived from said hydrophilic component distributed throughout said silicone polymer material in an amount effective to provide enhanced hydrophilicity to said silicone polymer material relative to said silicone polymeric material, provided said subjecting is ineffective to increase or decrease the degree of polymerization or the degree of cross-linking of said silicone polymeric material, and said silicone polymer material is utilized without further substantial polymerization or cross-linking.

6. The method of claim 5 wherein said silicone polymeric material is cross-linked and solid, and said introducing and subjecting are effective to distribute said hydrophilic constituent uniformly throughout said silicone polymer material.

7. The method of claim 5 wherein said silicone polymer material is optically clear and elastomeric, and which method further comprises forming said silicone polymer material into an optic of a foldable intraocular lens.

8. A method for incorporating a hydrophilic constituent into a silicone polymer material which comprises:

forming a precursor mixture containing two or more silicon-containing components in amounts effective to polymerize and form a silicone polymeric material, and a hydrophilic component including a hydrophilic portion and a silicone polymer portion; and subjecting said precursor mixture to conditions effective to polymerize said two or more silicon-containing components, immobilize said hydrophilic component or a hydrophilic derivative thereof, and form a silicone polymer material which is optically clear and sufficiently elastomeric to form an optic of a foldable intraocular lens and includes a hydrophilic constituent in an amount effective to provide enhanced hydrophilicity to said silicone polymer material relative to a substantially identical silicone polymer material without said hydrophilic constituent.

9. The method of claim 8 wherein said silicone polymer material is cross-linked and solid, and includes a covalently bonded hydrophilic constituent derived from said hydrophilic component.

10. The method of claim 8 wherein said silicone polymer material comprises an optically clear, addition-cure, cross-linked polysiloxane polymer, and which further comprises forming said silicone polymer material into an optic of a foldable intraocular lens.

11. A foldable intraocular lens comprising a foldable optic including an optically clear silicone polymer material being sufficiently elastomeric to form said optic of said foldable intraocular lens and including immobilized a hydrophilic constituent selected from the group consisting of a hydrophilic component and a hydrophilic derivative thereof in an amount effective to provide increased hydrophilicity to said silicone polymer material relative to a substantially identical polymer material without said hydrophilic constituent, said hydrophilic component including a hydrophilic portion and a silicone polymer portion, said hydrophilic constituent being distributed throughout and immobilized in said silicone polymer material without an increase or decrease in the degree of polymerization or the degree of cross-linking of said silicone polymer material, and said silicone polymer material is utilized without further substantial polymerization or cross-linking.

12. The foldable intraocular lens of claim 11 wherein said hydrophilic constituent is covalently bonded in said silicone polymer material.

13. The foldable intraocular lens of claim 11 wherein said hydrophilic constituent is distributed uniformly throughout said silicone polymer material, and is physically immobilized in said silicone polymer material.

14. A composition comprising an optically clear silicone polymer material which is sufficiently elastomeric to produce an optic of a foldable intraocular lens and includes an immobilized hydrophilic constituent selected from the group consisting of a hydrophilic component and a hydrophilic derivative thereof in an amount effective to provide increased hydrophilicity to said silicone polymer material relative to a substantially identical polymer material without said hydrophilic constituent, said hydrophilic component including a hydrophilic portion and a silicone polymer portion, said hydrophilic constituent being uniformly distributed throughout and immobilized in said silicone polymer material without an increase or decrease in the degree of polymerization or the degree of cross-linking of said silicone polymer material, and said silicone polymer material is utilized without further substantial polymerization or cross-linking.

15. The composition of claim 14 wherein said hydrophilic constituent is covalently bonded in said silicone polymer material.

16. The composition of claim 14 wherein said hydrophilic constituent is distributed uniformly throughout said silicone polymer material, and is physically immobilized in said silicone polymer material.

* * * * *

UNITED STATES PATENT AND TRADEMARK OFFICE
CERTIFICATE OF CORRECTION

PATENT NO. : 5,397,848
DATED : March 14, 1995
INVENTOR(S) : Yang et al

It is certified that error appears in the above-indentified patent and that said Letters Patent is hereby corrected as shown below:

Title page, item [63], RELATED U.S. APPLICATION DATA; delete "Oct. 13, 1992," and insert in place thereof --Oct. 9, 1992,--.

Column 11, line 11; delete "450" and insert in place thereof --45°--.

Signed and Sealed this

Twenty-first Day of January, 1997

Attest:

BRUCE LEHMAN

*Attesting Officer*     *Commissioner of Patents and Trademarks*